United States Patent
Carlson (10) Patent No.: US 9,759,679 B2
(45) Date of Patent: Sep. 12, 2017

(54) FLUID SENSOR WITH BACKSIDE OF SENSOR DIE CONTACTING HEADER

(71) Applicant: Honeywell International Inc., Morristown, NJ (US)

(72) Inventor: Robert Jon Carlson, Brooklyn Park, MN (US)

(73) Assignee: Honeywell International Inc., Morris Plains, NJ (US)

( * ) Notice: Subject to any disclaimer, the term of this patent is extended or adjusted under 35 U.S.C. 154(b) by 3 days.

(21) Appl. No.: 14/175,233

(22) Filed: Feb. 7, 2014

(65) Prior Publication Data
US 2015/0226698 A1    Aug. 13, 2015

(51) Int. Cl.
*H01L 29/49* (2006.01)
*G01N 27/414* (2006.01)
*B81B 7/00* (2006.01)

(52) U.S. Cl.
CPC .......... *G01N 27/414* (2013.01); *B81B 7/007* (2013.01)

(58) Field of Classification Search
CPC ...... G01N 27/414; H01L 23/12; H01L 23/147
See application file for complete search history.

(56) References Cited

U.S. PATENT DOCUMENTS

| | | | |
|---|---|---|---|
| 4,505,799 A * | 3/1985 | Baxter | 204/416 |
| 8,143,689 B2 | 3/2012 | Warsop et al. | |
| 8,186,226 B2 | 5/2012 | Ricks | |
| 8,402,835 B2 | 3/2013 | August et al. | |
| 8,624,371 B2 | 1/2014 | Bolken et al. | |
| 2004/0112633 A1* | 6/2004 | Endo et al. | 174/255 |
| 2008/0070333 A1* | 3/2008 | Morita | B29C 33/68 438/26 |
| 2009/0051012 A1* | 2/2009 | Maebashi | H01L 21/76898 257/621 |
| 2010/0140089 A1 | 6/2010 | Chou et al. | |
| 2012/0273845 A1 | 11/2012 | Brown et al. | |

(Continued)

FOREIGN PATENT DOCUMENTS

| | | |
|---|---|---|
| EP | 2482310 | 8/2012 |
| EP | 2518483 | 10/2012 |
| JP | H10227759 | 8/1998 |

OTHER PUBLICATIONS

Centre for High Performance Integrated Technologies and Systems Mar. 1997.*

(Continued)

*Primary Examiner* — Michael Shingleton
(74) *Attorney, Agent, or Firm* — Fogg & Powers LLC (57) ABSTRACT

Embodiments described herein provide for a sensing device including a sensor die attached to a header. The header has a first working surface composed of a first one or more electrically conductive pads and a bulk of the header. The sensor die has a second working surface and a third surface reverse of the second working surface. The sensor die includes a sensing element on the second working surface, and the third surface of the sensor die is composed of a second one or more electrically conductive pads and a dielectric layer. The first one or more electrically conductive pads of the header contact the second one or more electrically conductive pads of the sensor die, and the bulk of the header at the first working surface of the header contacts the dielectric layer of the third surface of the sensor die.

14 Claims, 3 Drawing Sheets

(56) References Cited

U.S. PATENT DOCUMENTS

2013/0164466 A1 6/2013 Khadilkar et al.
2015/0028396 A1 1/2015 Horkheimer et al.

OTHER PUBLICATIONS

European Patent Office, "Office Action for EP Application No. 14167596.7 dated Dec. 8, 2014", "for Foreign Counterpart to U.S. Appl. No. 13/952,888", dated Dec. 8, 2014, pp. 1-10, Published in: EP.

Kyo et al., "Trial of Hydrothermal Plume Sensing Using Newly Developed ISFET pH Sensor", "IEEE Proceedings: Celebrating the Past, Temaing Toward the Future", Sep. 22, 2003, pp. 1732-1737, Publisher: IEEE, Published in: San Diego, CA.

Venkatesan et al., "Study on Behavior of Carbon Fiber-Reinforced Composite for Deep Sea Applications", "2002 Offshore Technology Conference", May 9, 2002, pp. 1-9, Published in: Houston, TX.

Sverdlov, "Chapter 2: Scaling, Power Consumption, and Mobility Enhancement Techniques", "Strain-Induced Effects in Advanced MOSFETs; at least as early as Dec. 2011", 2011, pp. 5-22, Publisher: Springer-Verlag.

Arghavani et al., "A Reliable and Manufacturable Method to Induce a Stress of >1 GPa on a P-Channel MOSFET in High Volume Manufacturing", "IEEE Electron Device Letters", Feb. 2006, pp. 114-116, vol. 27, No. 2.

Barlian et al., "Review: Semiconductor Piezoresistance for Microsystems", "Proceedings of the IEEE", Apr. 1, 2009, pp. 513-552, vol. 97, No. 3, Publisher: IEEE.

Chang et al., "Piezoresistive Sensor of Short-and Long-Channel MOSFETs on (100) Silicon", Dec. 19, 2008, pp. 1-4, Publisher: IEEE.

Hopcroft et al., "What is the Young's Modulus of Silicon", "Journal of Microelectromechanical Systems", Apr. 2010, pp. 229-238, vol. 19, No. 2.

Song et al., "Development of In-situ Laser Vacuum Annealing and Sealing Processes for an Application to Field Emission Displays", "Vacuum Microelectronics Conference, 2001. IVMC 2001. Proceedings of the 14th International", Aug. 2001, pp. 219-220.

Sun et al., "Strain Effect in Semiconductors", "at least as early as Dec. 2010", 2010, pp. 1-10, Publisher: Springer Science + Business Media, LLC.

Thompson et al., "Uniaxial-Process-Induced Strained-Si: Extending the CMOS Roadmap", "IEEE Transactions on Electron Devices", May 2006, pp. 1010-1020, vol. 53, No. 5.

Thompson et al., "Future of Strained Si/Semiconductors in Nanoscale MOSFETs", Sep. 2006, pp. 1-4, Publisher: University of Florida.

Wu et al., "Glass Frit as a Hermetic Joining Layer in Laser Based Joining of Miniature Devices", "IEEE Transactions on Components and Packaging Technologies", Jun. 2010, pp. 470-477, vol. 33, No. 2.

U.S., "Restriction Requirement", "from U.S. Appl. No. 13/952,888", dated Sep. 4, 2014, pp. 1-7, Published in: US.

European Patent Office, "Extended European Search Report from EP Application No. 15152414.7 dated Dec. 18, 2015", "from Foreign Counterpart of U.S. Appl. No. 14/175,233", dated Dec. 18, 2015, pp. 1-6, Published in: EP.

Huang et al., "A New Structured ISFET With Integrated TI/PD/AG/AFCI Electrode and Micromachined Back-Side P+ Contacts", "Journal of the Chinese Institute of Engineers", Mar. 3, 2011, pp. 327-334, vol. 25, No. 3, Published in: CN.

U.S., "Final Office Action", "from U.S. Appl. No. 13/952,888", dated Nov. 25, 2015, pp. 1-23, Published in: US.

U.S., "Advisory Action", "U.S. Appl. No. 13/952,888", dated Feb. 9, 2016, pp. 1-5, Published in: US.

U.S., "Notice of Allowance", "U.S. Appl. No. 13/952,888", dated Jul. 7, 2016, pp. 1-22, Published in: US.

U.S. Patent and Trademark Office, "Office Action", "from U.S. Appl. No. 13/952,888", dated May 27, 2015, pp. 1-28, Published in: US.

\* cited by examiner

FLUID SENSOR WITH BACKSIDE OF SENSOR DIE CONTACTING HEADER

BACKGROUND

Some conventional fluid sensing devices have a sensor die with a sensing element on a first surface thereof. In order to enable good fluid flow to the sensing element, electrical contacts for the sensing element are located on the backside of the sensor die. The backside contacts can be coupled to the sensing element by electrical pins that extend into the sensor die from the backside and couple to the sensing element. Bondwires are coupled to the backside contacts to interconnect the backside contacts with other components in and/or outside of the sensor package.

Mechanical support for the sensor die is provided by a header of a sensor package. The header includes one or more legs that extend around and define a cavity. The sensor die is mounted to the one or more legs such that the one or more legs attach near the outer edge of the sensor die and the cavity in between the one or more legs is between a portion of the backside of the sensor die and the header. The bondwires are coupled to the backside contacts with the cavity, and extend through the cavity to couple to an appropriate other location within the sensor package.

SUMMARY

Embodiments described herein provide for a sensing device including a sensor die attached to a header. The header has a first working surface composed of a first one or more electrically conductive pads and a bulk of the header. The sensor die has a second working surface and a third surface reverse of the second working surface. The sensor die includes a sensing element on the second working surface, one or more electrically conductive doped regions proximate the sensing element, and one or more electrically conductive pins extending from the third surface partially through the sensor die into the one or more electrically conductive doped regions. The third surface of the sensor die is composed of a second one or more electrically conductive pads and a dielectric layer. Additionally, the first one or more electrically conductive pads of the header contact the second one or more electrically conductive pads of the sensor die, and the bulk of the header at the first working surface of the header contacts the dielectric layer of the third surface of the sensor die.

DRAWINGS

In accordance with common practice, the various described features are not drawn to scale but are drawn to emphasize features relevant to the present description. Reference characters denote like elements throughout figures and text.

DETAILED DESCRIPTION

A sensing element that is fabricated on a silicon substrate can experience piezo resistive effects when the silicon substrate is bent or stressed. The piezo resistive effects can cause the electrical properties of the sensing element to change. For conventional sensing devices that are used in a high pressure and/or a variable pressure environment, the cavity between the sensor die and the header can allow sufficient bending or stressing of the sensor die such that the piezo resistive effects are significant.

Figure 1:
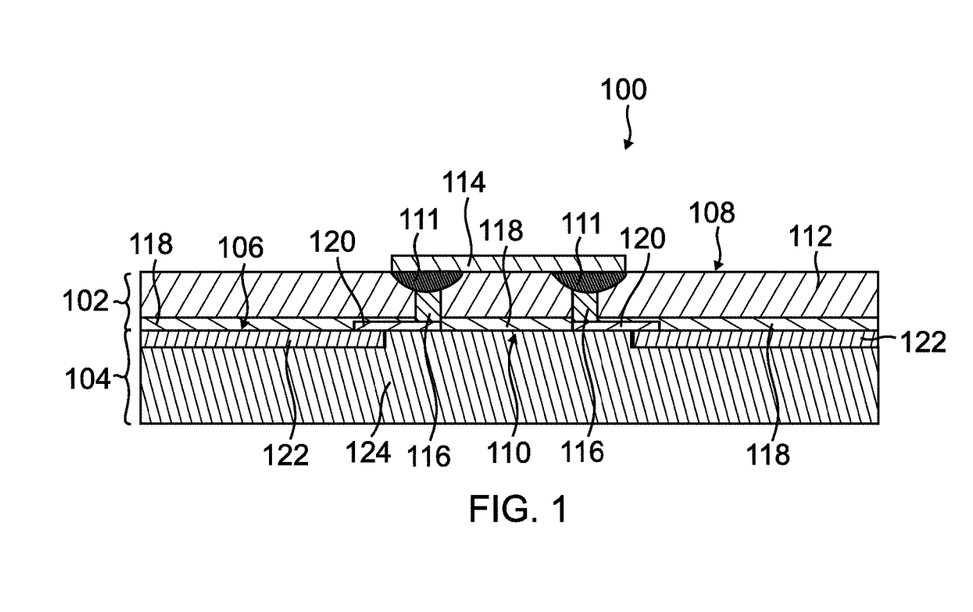
FIG. 1 is a cross-sectional view of a portion of an example sensing device having a sensor die attached to a package header.

FIG. 1 is a cross-sectional view of a portion of an example sensing device 100. The sensing device 100 includes a sensor die 102 attached to a package header 104. The header 104 provides mechanical support for the sensor die 102. The header 104 has a first working surface 106. The sensor die 102 has a generally planar structure defining a second (major) working surface 108, a third (major) surface 110 (also referred to herein as the "backside") which is reverse of the second surface 108. The sensor die 102 also includes one or more edges around the sides between the second surface 108 and the third surface 110. The third surface 110 of the sensor die 102 is attached to the first surface 106 of the header 104.

The sensor die 102 includes a monolithic substrate 112 having a sensing element 114 fabricated therein. The sensing element 114 is fabricated in the second surface 110 of the sensor die 102. In an example, the sensing element 114 is a fluid sensor that is configured to sense a property of a fluid. For example, the sensing element 114 can be a pH sensor, a pressure sensor, an oxygen sensor, a conductivity sensor, a flow sensor, or another fluid sensor. In an implementation of such a fluid sensor, the sensor die 102 is an ISFET die and the sensing element 114 an ion sensor for sensing a pH of a fluid in contact therewith. The sensing device 100 is configured such that the sensing element 114 can be exposed to a fluid (e.g., sea or ocean water) in order to measure a property of the fluid.

The sensor die 102 also includes one or more electrically conductive pins 116 extending from the third surface 110 partially through the substrate 112 to meet with one or more electrically conductive doped regions 111 proximate the second surface 108 and the sensing element 114. The one or more electrically conductive pins 116 are electrically coupled to the sensing element 114 via the one or more electrically conductive doped regions 111. In an example, the one or more electrically conductive pins 116 are composed of one of gold (Au) or platinum (Pt). As is common in the art, a dielectric layer (not shown) is disposed between the electrically conductive pins 116 and the substrate 112 to electrically isolate the electrically conductive pins 116 from the substrate 112. The one or more electrically conductive pins 116 can have any suitable geometry such as a cylindrical (e.g., a straight wall) or a pyramidal (e.g., a sloped wall) geometry.

The sensor die 102 also includes a dielectric layer 118 in the third surface 110. In an example, the substrate 112 is composed of silicon and the dielectric layer 118 is composed of silicon dioxide. The sensor die 102 also includes a first one or more electrically conductive pads 120 forming a part of the third surface 110. In particular, an outer surface of the first one or more electrically conductive pads 120 and an outer surface of the dielectric layer 118 define the third surface 110 of the sensor die 102. That is, the third surface 110 of the sensor die 102 is composed of an outer surface of the first one or more electrically conductive pads 120 and an outer surface of the dielectric layer 118. In an example, the dielectric layer 118 and the first one or more electrically conductive pads 120 form the entire backside 110 of the sensor die 102. That is, in such an example, the dielectric layer 118 and the first one or more electrically conductive pads 120 are the only exposed components on the backside 110.

A second one or more electrically conductive pads 122 form a part of the first surface 106 of the header 104. In particular, an outer surface of the second one or more electrically conductive pads 122 and an outer surface of the bulk 124 of the header 104 define the first surface 106 of the header 104. That is, the first surface 106 of the header 104 is composed of an outer surface of the second one or more electrically conductive pads 122 and an outer surface of the bulk 124 of the header 104. In an example, the header 104 can be laterally wider than the sensor die 102 such that the first surface 106 of the header 104 extends beyond the edges of the sensor die 102. In an implementation of such an example, the second one or more electrically conductive pads 122 can extend laterally outward from the edges of the sensor die 102 to form conductive pads for coupling the second one or more electrically conductive pads 122 to other components. In an example, the bulk 124 of the header 104 is composed of a ceramic, such as aluminum oxide or aluminum nitride.

The first one or more electrically conductive pads 120 and the second one or more electrically conductive pads 122 are disposed to contact one another while the sensor die 102 is attached to the header 104. This contact between the first one or more electrically conductive pads 120 and the second one or more electrically conductive pads 122 provides electrical coupling for the sensing element 114 through the backside 110 of the sensor die 102 to other components within and/or external to the sensing device 100. Additionally, in some examples, the first one or more electrically conductive pads 120 are bonded to the second one or more electrically conductive pads 122 to attach the sensor die 102 to the header 104. For example, the first one or more electrically conductive pads 120 and the second one or more electrically conductive pads 122 can be composed of gold (Au) such that the contacting conductive pads 120, 122 will bond easily. In another example the first one or more electrically conductive pads 120 and the second one or more electrically conductive pads 122 are composed of platinum (Pt).

The first surface 106 and the third surface 110 have geometries that mate with one another such while that the first one or more electrically conductive pads 120 contact the second one or more electrically conductive pads 122, the dielectric layer 118 at the third surface 110 contacts the bulk 124 of the header 102 at the first surface 106. This contact between the surfaces 106, 110 eliminates the cavity between the backside of the sensor die and the header that is present in conventional sensing devices. Moreover, this contact provides increased support for the sensor die 102 to reduce bending and flexing of the sensor die 102 when pressure is present on the second surface 108. In an example, the entire third surface 110 (backside) of the sensor die 102 contacts the first surface 106 of the header 104. In this way, the sensor die 102 can be attached to the header 104, electrical coupling of the sensing element 114 can be provided through the backside 110 of the sensor die 102, and the backside 110 of the sensor die 102 can be supported by the header 102. In addition, in examples where the first one or more conductive pads 120 and the second one or more conductive pads 122 are gold, the malleability of the gold bond between the pads 120, 122 can provide lateral flexibility enabling the sensor die 102 to expand and/or contract relative to the header 106 without detaching therefrom.

In an example, the third surface 110 is substantially flat and the first surface 106 is substantially flat at least in an area in which the sensor die 102 is opposite thereof. These flat surfaces 106, 110 enable the mating between the surfaces. Such an example is illustrated in FIG. 1. In some implementations of such an example, the area of the first surface 106 beyond the edges of the sensor die 102 can be planar with the area of the first surface 106 under the sensor die 102. In other implementations, the area of the first surface 106 beyond the edges of the sensor die 102 can have non-planar portions such as conductive pads or other components.

In such an example where the third surface 110 and at least part of the first surface 106 is substantially flat, the first one or more electrically conductive pads 120 are inlaid into the dielectric layer 118 and the second one or more electrically conductive pads 122 are inlaid into the bulk 124 of the header 110 to enable the third surface 110 and the first surface 106 to be substantially flat. In an example, no solder (e.g., a solder ball) or other electrical and/or physical coupling material is used to couple or attach the first one or more electrically conductive pads 120 to the second one or more electrically conductive pads 122. Since there is no such coupling material used, areas on the third surface 110 of the sensor die 102 other than the first one or more electrically conductive pads 120 can contact corresponding areas on first surface 106. Accordingly, such a configuration having flat surfaces 106, 110 that contact one another provides increased support to the sensor die 102. In an implementation of such an example where the first surface 106 and the third surface 110 are substantially flat, the outer surface of the first one or more electrically conductive pads 120 is raised slightly higher than the outer surface of the dielectric layer 118 making up the third surface. The slightly raised outer surface of the first one or more electrically conductive pads 120 accounts for the fact that the first one or more electrically conductive pads 120 will squish slightly during contact with the second one or more electrically conductive pads 122. Since the first one or more electrically conductive pads 120 is slightly raised with respect to the rest of the third surface 110, sufficient contact and bonding can occur between the first one or more electrically conductive pads 120 and the second one or more electrically conductive pads 122 even after the first one or more electrically conductive pads 120 and/or second one or more electrically conductive pads 122 are slightly squished. In some implementations, in addition to or instead of the first one or more electrically conductive pads 120 being slightly raised, the second one or more conductive pads 122 can be slightly raised with respect to the outer surface of the bulk 124 of the header 104 at the first surface 106. The first one or more electrically conductive pads 120 and the second one or more electrically conductive pads 122 can be raised up to 1 micron higher than the adjacent surfaces. In a particular example the first one or more electrically conductive pads 120 and the second one or more electrically conductive pads 122 can be raised up to 1000 Angstroms higher than the adjacent surfaces.

In an alternative example, neither the first surface 106 nor the third surface 110 are flat, however, the geometries of the surfaces 106, 110 are coordinated (matched) such that the surfaces 106, 110 mate with one another and enable the first one or more electrically conductive pads 120 to contact the second one or more electrically conductive pads 122 while the dielectric layer 118 at the third surface 110 contacts the bulk 124 of the header 102 at the first surface 106. In an implementation of such an example, first one or more electrically conductive pads 120 can extend above the outer surface of the dielectric layer 118 at the third surface 110 and the bulk 124 of the header 104 at the first surface 106 can extend a corresponding amount above the outer surface of the second one or more electrically conductive pads 122 to mate with the geometry of third surface 110. Other geometries are also possible.

FIGS. 2A-2E are cross-sectional views of example stages during manufacturing of a sensing device 100. Notably, some or all of the fabrication acts to form the sensor die 102 can occur at the wafer level on a wafer prior to singulation. That is, some or all of the fabrication acts to form the sensor die 102 can be performed multiple times in parallel to fabricate multiple sensor dies 102 on a single wafer. The below description relates the process of fabricating a single sensing device 100, a single sensor die 102, and a single header 104; however, it should be understood the below acts can occur at the wafer level as described above. Additionally, the below stages shown in FIGS. 2A-2E correspond to an example where the third surface 110 and the first surface 106 are substantially flat, however, it should be understood that in other examples, the first surface 106 and the third surface 110 are not substantially flat.

Figure 2A:
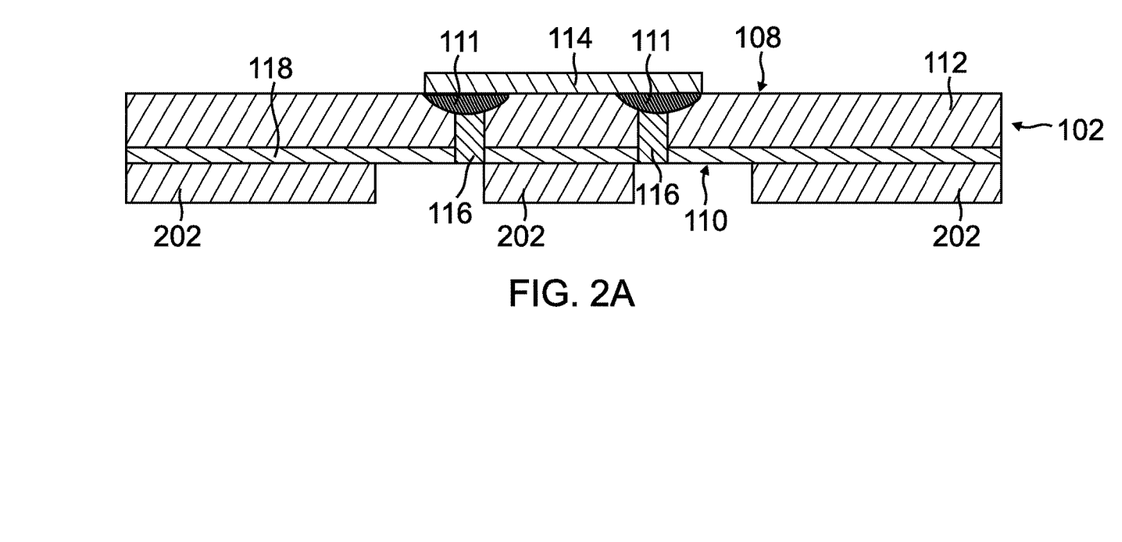
FIGS. 2A-2E are cross-sectional views of example stages during manufacturing of the sensing device of FIG. 1.

As shown in FIG. 2A, the second surface 108 of a substrate 112 can be doped to form one or more doped regions 111. The sensing element 114 and the one or more electrically conductive pins 116 can also be fabricated in the substrate 112. The sensing element 114 can be fabricated on the second working surface 108 of the substrate 112 and the one or more electrically conductive pins 116 can be fabricated from the third surface 110 partially through the substrate 112 to the one or more doped regions 111. The electrically conductive pins 116 can be formed by depositing a dielectric layer and electrical conductors in an etch in the third surface 110, and the electrical conductors can be formed such that they are electrically coupled to the sensing element 114 via the one or more doped regions 111. Such fabrication techniques are known in the art. The substrate 112 can either be provided with a dielectric layer 118, or a dielectric layer 118 can be formed on the backside 110 thereof in any suitable manner.

The first one or more electrically conductive pads 120 can be fabricated on the dielectric layer 118 on the backside 110 of the substrate 112. In examples where the backside 110 is substantially flat as shown in FIG. 1, the first one or more electrically conductive pads 120 can be inlaid into the dielectric layer 118. To inlay the first one or more electrically conductive pads 120 into the dielectric layer 118, photoresist 202 can be applied on areas of the dielectric layer 118 in which the inlaid electrical conductors 120 will not be present as shown in FIG. 2A. In particular, the photoresist 202 can be applied such that the inlaid electrical conductors 120 are coupled to the electrical conductors in the electrically conductive pins 116 and are disposed to contact one or more second inlaid electrical conductors in the header 104.

Figure 2B:
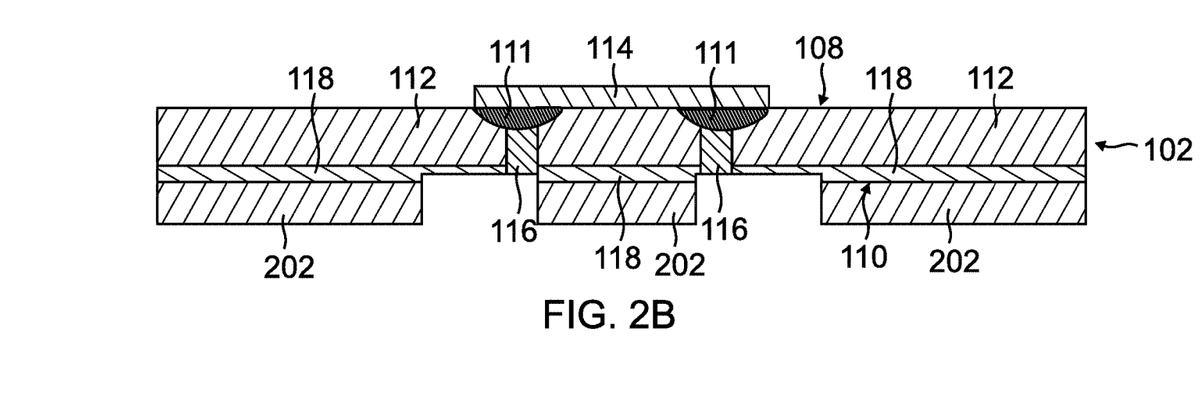

Once the photoresist 202 has been deposited, one or more recesses can be etched in the dielectric layer 118 in the gaps provided in the photoresist 202 as shown in FIG. 2B. The one or more recesses are etched into the dielectric layer 118 such that a layer of dielectric remains in the bottom of the trenches. That is, etching does not etch all the way through dielectric layer 118 to the substrate 112. This ensures that a layer dielectric provides electrically insulation for the first one or more electrically conductive pads 120 from the substrate 112. In some examples, the dielectric layer 118 is thicker than in conventional sensors to provide adequate depth for fabricating the first one or more electrically conductive pads 120 while leaving a layer of dielectric beneath the first one or more electrically conductive pads 120.

Figure 2C:
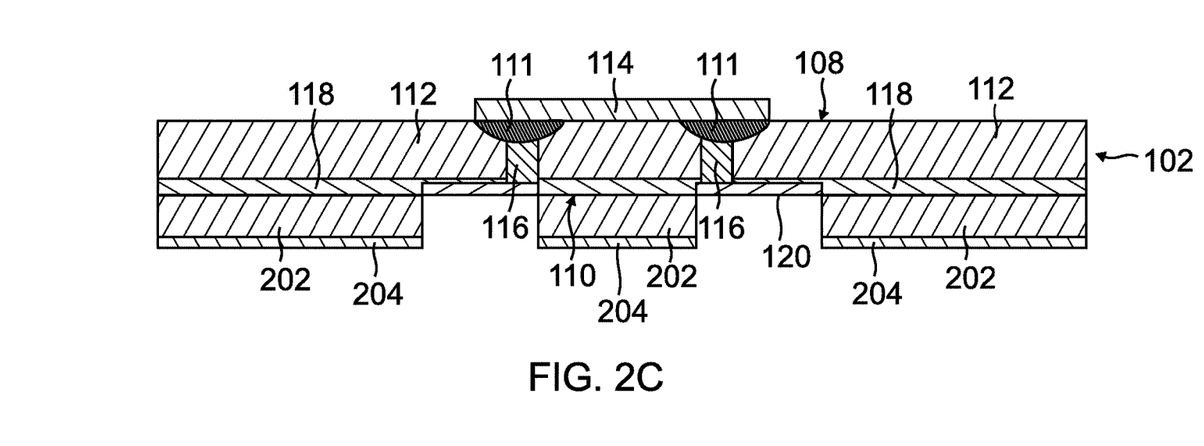
Figure 2D:
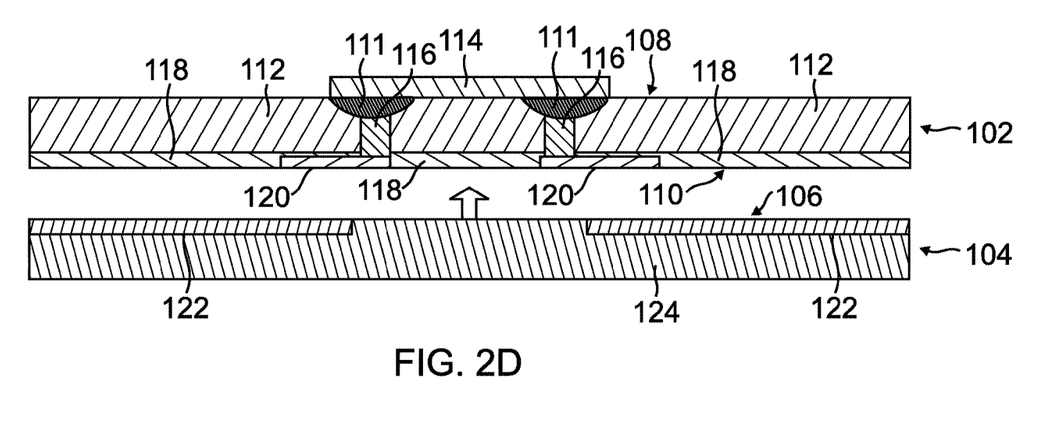

Once the recess have been etched, the electrically conductive material 204 (e.g., a metal such as gold (Au) or platinum (Pt)) can be deposited on the backside 110 of the substrate 112 in order to place electrically conductive material in one or more recesses as shown in FIG. 2C. Once the electrically conductive material 204 is deposited into the one or more recesses, the photoresist 202 can be removed along with the electrically conductive material 204 on the photoresist 202. After removal of the photoresist 202, the first one or more electrically conductive pads 120 remain in the third surface 110 of the sensor die 102 as shown in FIG. 2D.

The outer surface of the first one or more electrically conductive pads 120 is slightly raised with respect to the outer surface of the dielectric layer 118 by controlling the depositing of the electrically conductive material 204 into the one or more recesses (FIG. 2C). In a second example, the outer surface of the first one or more electrically conductive pads 120 is made co-planar with the outer surface of the dielectric layer 118 by processing the backside 110 of the substrate 112 after removal of the photoresist 202 (FIG. 2D). Such processing can include grinding or polishing for example. In a third example both the controlled deposition and processing of the backside 110 are used to form an outer surface of the first one or more electrically conductive pads 120 that is co-planar with an outer surface of the dielectric layer 118.

The second one or more electrically conductive pads 122 are fabricated on the header 104 in any suitable manner such as in a manner similar to that described above for the first one or more electrically conductive pads 120 of the sensor die 102. For example, one or more recesses can be etched in the bulk 124 of the header 104 at the first surface 106 in the areas in which the second one or more electrically conductive pads are to be present. Electrically conductive material can then be deposited in the one or more recesses to form the second one or more electrically conductive pads. The second one or more electrically conductive pads 122 can be fabricated such that an outer surface of the second one or more electrically conductive pads 122 is co-planar with an outer surface of a bulk 124 of the header 104 at the first surface 106.

In a first example, the outer surface of the second one or more electrically conductive pads 122 is raised slightly with respect the outer surface of the bulk 124 of the header 104 by controlling the depositing of the electrically conductive material into the one or more recesses. In a second example, the outer surface of the second one or more electrically conductive pads 122 is made co-planar with the outer surface of the bulk 124 of the header 104 by processing the first surface 106 of the header 104 after depositing the electrically conductive material. Such processing can include grinding or polishing for example. In a third example both the controlled deposition and processing of the first surface 106 are used to form an outer surface of the second one or more electrically conductive pads 122 that is co-planar with an outer surface of the bulk 124 of the header 104.

Figure 2E:
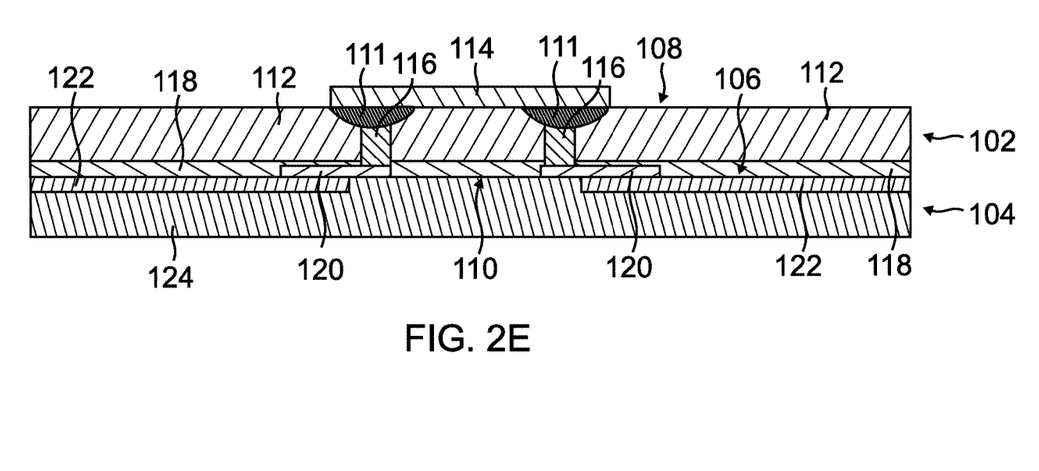

Once the first one or more electrically conductive pads 120 and the second one or more electrically conductive pads 122 are fabricated, the third surface 110 of the sensor die 102 can be attached to the first surface 106 of the header 104 such that the first one or more electrically conductive pads 120 contact the second one or more electrically conductive pads 122 as shown in FIGS. 2D and 2E. In an example, the first one or more electrically conductive pads 120 can be bonded to the second one or more electrically conductive pads 122. Such bonding include one or more of heating the first one or more electrically conductive pads 120 and the second one or more electrically conductive pads 122 while they are in contact, applying ultrasonic energy to the first one or more electrically conductive pads 120 and the second one or more electrically conductive pads 122 while they are in contact, and pressing the first one or more electrically conductive pads 120 and the second one or more electrically conductive pads 122 together.

Example Embodiments

Example 1 includes a sensing device comprising: a header having a first working surface thereof, the first working surface composed of a first one or more electrically conductive pads and a bulk of the header; a sensor die attached to the header, the sensor die having a second working surface and a third surface reverse of the second working surface, the sensor die including: a sensing element on the second working surface; one or more electrically conductive doped regions proximate the sensing element; and one or more electrically conductive pins extending from the third surface partially through the sensor die into the one or more electrically conductive doped regions; wherein the third surface of the sensor die is composed of a second one or more electrically conductive pads and a dielectric layer, wherein the first one or more electrically conductive pads of the header contact the second one or more electrically conductive pads of the sensor die, and wherein the bulk of the header at the first working surface of the header contacts the dielectric layer of the third surface of the sensor die.

Example 2 includes the sensing device of Example 1, wherein the sensor die is an ion sensitive field effect transistor (ISFET) die, and wherein the sensing element is an ion sensor that responds to pH, wherein the ion sensor is configured to be exposed to a fluid, and wherein the ion sensor outputs a signal related to a pH level of the fluid, and the signal propagates through the at least one of the one or more electrically conductive pins, at least one of the second one or more electrically conductive pads, and at least one of the first one or more electrically conductive pads.

Example 3 includes the sensing device of any of Examples 1-2, wherein sensor die is composed of silicon, and wherein the dielectric layer is composed of silicon dioxide.

Example 4 includes the sensing device of any of Examples 1-3, wherein the bulk of the header is composed of a ceramic.

Example 5 includes the sensing device of any of Examples 1-4, wherein the first one or more electrically conductive pads and the second one or more electrically conductive pads are composed of one of gold or platinum.

Example 6 includes the sensing device of Example 5, wherein the first one or more electrically conductive pads and the second one or more electrically conductive pads are bonded together.

Example 7 includes the sensing device of any of Examples 1-6, wherein the first one or more electrically conductive pads are inlaid into the bulk of the header and the second one or more electrically conductive pads are inlaid into the dielectric layer.

Example 8 includes the sensing device of any of Examples 1-7, wherein the header extends laterally wider than the sensor die, and wherein the first one or more electrically conductive pads extend laterally outward of the sensor die and form pads for coupling to other components.

Example 9 includes the sensing device of any of Examples 1-8, wherein the sensing element is configured to sense a property of a fluid.

Example 10 includes the sensing device of Example 9, wherein the sensing element is one of a pH sensor, a pressure sensor, an oxygen sensor, or a conductivity sensor.

Example 11 includes a method of manufacturing a sensing device, the method comprising: fabricating a first one or more electrically conductive pads in a first working surface of a header such that the first working surface is composed of the first one or more electrical conductors and a bulk of the header; doping a second working surface of a substrate to form one or more electrically conductive doped regions proximate the second working surface; fabricating a sensing element in the second working surface of the substrate, wherein the substrate has a third surface reverse of the second working surface, wherein the third surface is composed of a dielectric layer; fabricating one or more electrically conductive pins in the third surface of the substrate such that the electrically conductive pins extending partially through the substrate and couple to the one or more electrically conductive doped regions; fabricating a second one or more electrically conductive pads in a third surface of the substrate, the second one or more electrically conductive pads coupled to the one or more electrically conductive pins such that the third surface is composed of the second one or more electrically conductive pads and the dielectric layer; and attaching the third surface of the sensor die to the first working surface of the header such that the first one or more electrically conductive pads contact the second one or more electrically conductive pads and the bulk of the header at the first working surface of the header is configured contacts the dielectric layer of the third surface of the sensor die.

Example 12 includes the method of Example 11, comprising bonding the first one or more electrically conductive pads to the second one or more electrically conductive pads.

Example 13 includes the method of Example 12, wherein the first one or more electrically conductive pads and the second one or more electrically conductive pads are composed of one of gold or platinum, wherein bonding includes at least one of heating the first one or more electrically conductive pads and the second one or more electrically conductive pads while they are in contact, applying ultrasonic energy to the first one or more electrically conductive pads and the second one or more electrically conductive pads while they are in contact, and pressing the first one or more electrically conductive pads and the second one or more electrically conductive pads together.

Example 14 includes the method of any of Examples 11-13, wherein fabricating a first one or more electrically conductive pads includes: etching one or more recesses in the bulk of the header at the first working surface; and depositing electrically conductive material in the one or more recesses.

Example 15 includes the method of any of Examples 11-14, wherein fabricating a second one or more electrically conductive pads includes: etching one or more recesses in the dielectric layer; and depositing electrically conductive material in the one or more recesses.

Example 16 includes a sensing device comprising: a header having a first one or more electrically conductive pads, wherein the first one or more electrically conductive pads and a bulk of the header define a first surface of the header, wherein the first surface is flat; a sensor die attached to the header, the sensor die having a second surface and a third surface reverse of the second surface, the sensor die including: a sensing element in a second surface; one or more through wafer vias having an electrical conductor therein, wherein the electrical conductor is coupled to the sensing element; a dielectric layer; a second one or more electrically conductive pads coupled to the one or more through wafer vias, wherein the second one or more electrically conductive pads and the dielectric layer define the third surface of the sensor die, wherein the third surface is flat; wherein the third surface of the sensor dies is attached to the first surface of the header, wherein the first one or more electrically conductive pads contact the second one or more inlaid conductors.

Example 17 includes the sensing device of Example 16, wherein the sensor die is an ion sensitive field effect transistor (ISFET) die, and wherein the sensing element is an ion sensor that responds to pH, wherein the ion sensor is configured to be exposed to a fluid, and wherein the ion sensor outputs a signal related to a pH level of the fluid, and the signal propagates through at least one of the one or more through wafer vias, at least one of the second one or more electrically conductive pads, and at least one of the first one or more electrically conductive pads.

Example 18 includes the sensing device of any of Examples 16-17, wherein the sensor die is composed of silicon, the dielectric layer is composed of silicon dioxide, and the bulk of the header is composed of a ceramic.

Example 19 includes the sensing device of any of Examples 16-18, wherein the first one or more electrically conductive pads and the second one or more electrically conductive pads are composed of one of gold or platinum, wherein the first one or more electrically conductive pads and the second one or more electrically conductive pads are bonded together.

Example 20 includes the sensing device of any of Examples 16-19, wherein the sensing element is configured to sense a property of a fluid.

What is claimed is:

1. A sensing device comprising:
    a header having a first working surface thereof, the first working surface composed of a first one or more electrically conductive pads and a bulk of the header, wherein the first working surface is substantially flat;
    a sensor die attached to the header, the sensor die having a second working surface and a third surface reverse of the second working surface, the sensor die including:
        a sensing element on the second working surface;
        one or more electrically conductive doped regions proximate the sensing element; and
        one or more electrically conductive pins extending from the third surface partially through the sensor die into the one or more electrically conductive doped regions;
        wherein the third surface of the sensor die is composed of a second one or more electrically conductive pads and a dielectric layer, and wherein the third surface is substantially flat; and
    wherein the first working surface contacts the third surface such that contact between the first working surface and the third surface is cavity-free, wherein the first one or more electrically conductive pads of the header contact the second one or more electrically conductive pads of the sensor die, and wherein the bulk of the header at the first working surface of the header contacts the dielectric layer of the third surface of the sensor die.

2. The sensing device of claim 1, wherein the sensor die is an ion sensitive field effect transistor (ISFET) die, and wherein the sensing element is an ion sensor that responds to pH, wherein the ion sensor is configured to be exposed to a fluid, and wherein the ion sensor outputs a signal related to a pH level of the fluid, and the signal propagates through the at least one of the one or more electrically conductive pins, at least one of the second one or more electrically conductive pads, and at least one of the first one or more electrically conductive pads.

3. The sensing device of claim 1, wherein sensor die is composed of silicon, and wherein the dielectric layer is composed of silicon dioxide.

4. The sensing device of claim 1, wherein the bulk of the header is composed of a ceramic.

5. The sensing device of claim 1, wherein the first one or more electrically conductive pads and the second one or more electrically conductive pads are composed of one of gold or platinum.

6. The sensing device of claim 5, wherein the first one or more electrically conductive pads and the second one or more electrically conductive pads are bonded together.

7. The sensing device of claim 1, wherein the first one or more electrically conductive pads are inlaid into the bulk of the header and the second one or more electrically conductive pads are inlaid into the dielectric layer.

8. The sensing device of claim 1, wherein the header extends laterally wider than the sensor die, and wherein the first one or more electrically conductive pads extend laterally outward of the sensor die and form pads for coupling to other components.

9. The sensing device of claim 1, wherein the sensing element is configured to sense a property of a fluid.

10. A sensing device comprising:
    a header having a first one or more electrically conductive pads, wherein the first one or more electrically conductive pads and a bulk of the header define a first surface of the header, wherein the first surface is substantially flat;
    a sensor die attached to the header, the sensor die having a second surface and a third surface reverse of the second surface, the sensor die including:
    a sensing element in a second surface;
        one or more through wafer vias having an electrical conductor therein, wherein the electrical conductor is coupled to the sensing element;
        a dielectric layer;
        a second one or more electrically conductive pads coupled to the one or more through wafer vias,
        wherein the second one or more electrically conductive pads and the dielectric layer define the third surface of the sensor die, wherein the third surface is substantially flat;
    wherein the third surface of the sensor dies is attached to the first surface of the header such that contact between the first working surface and the third surface is cavity-free, wherein the first one or more electrically conductive pads contact the second one or more inlaid conductors.

11. The sensing device of claim 10, wherein the sensor die is an ion sensitive field effect transistor (ISFET) die, and wherein the sensing element is an ion sensor that responds to pH, wherein the ion sensor is configured to be exposed to a fluid, and wherein the ion sensor outputs a signal related to a pH level of the fluid, and the signal propagates through at least one of the one or more through wafer vias, at least one of the second one or more electrically conductive pads, and at least one of the first one or more electrically conductive pads.

12. The sensing device of claim 10, wherein the sensor die is composed of silicon, the dielectric layer is composed of silicon dioxide, and the bulk of the header is composed of a ceramic.

13. The sensing device of claim 10, wherein the first one or more electrically conductive pads and the second one or more electrically conductive pads are composed of one of gold or platinum, wherein the first one or more electrically conductive pads and the second one or more electrically conductive pads are bonded together.

14. The sensing device of claim 10, wherein the sensing element is configured to sense a property of a fluid.

\* \* \* \* \*